United States Patent [19]

Davidson et al.

[11] Patent Number: 5,387,511
[45] Date of Patent: Feb. 7, 1995

[54] **EXTRACTION PROCEDURE FOR *CHLAMYDIA* AND *NEISSERIA* ANTIGENS**

[75] Inventors: Ian W. Davidson, Bedfordshire; Paul Sheard, Northants, both of England

[73] Assignee: Unilever Patent Holdings B.V., Rotterdam, Netherlands

[21] Appl. No.: 911,378

[22] Filed: Jul. 13, 1992

Related U.S. Application Data

[63] Continuation of Ser. No. 623,971, filed as PCT/GP90/00568, Apr. 12, 1990, abandoned.

[30] Foreign Application Priority Data

Apr. 14, 1989 [GB] United Kingdom ............... 8908548
Mar. 5, 1990 [GB] United Kingdom ............... 9004845

[51] Int. Cl.$^6$ ..................... C12P 19/04; C12P 21/04
[52] U.S. Cl. .................................. 435/101; 435/71.2; 435/7.2; 435/7.32; 435/871
[58] Field of Search ............... 435/101, 7.2, 7.32, 435/71.2, 871; 436/554; 424/DIG. 6; 210/633, 638, 639, 647

[56] References Cited

U.S. PATENT DOCUMENTS 4,916,057  4/1990  Thompson et al. ............... 435/962

*Primary Examiner*—Douglas W. Robinson
*Attorney, Agent, or Firm*—Cushman Darby & Cushman

[57] ABSTRACT

Enhanced extraction of solubilized antigens is obtained from bacteria such as Chlamydia and Neisseri by the use of a buffer containing a zwitterionic surface active agent, especially CHAPS or CHAPSO, in the absence of divalent cations. The extraction is conducted at elevated temperature, and provides a sample useful in assays for the presence of the bacteria.

2 Claims, No Drawings

EXTRACTION PROCEDURE FOR *CHLAMYDIA* AND *NEISSERIA* ANTIGENS

This is a continuation of application Ser. No. 07/623,971, filed as PCT/GB90/00568, Apr. 12, 1990, now abandoned.

The present invention relates to procedures for extracting antigenic material in solubilised form from cellular biological materials such as bacteria. The solubilised antigenic material can be used thereafter in assay procedures to determine the presence or identity of the cellular material.

The use of surface active agents in extraction media at elevated temperature has been proposed. Examples are given in EP 167395 and EP 183383, both of which relate to extraction procedures especially applicable to species of Chlamydia.

EP 183383 says that it is beneficial to have divalent cations, specifically magnesium and zinc, present during the heating stage of an extraction procedure.

However, in complete contrast, we have found that a better extraction of antigenic material can be obtained in the absence of divalent cations.

The invention provides a procedure for extracting solubilised antigenic material from cellular biological material, such as bacteria, wherein the cellular material is treated with an aqueous solution of a surface active agent, the solution being substantially free from divalent cations. Preferably the surface active agent is zwitterionic. More preferably, the surface active agent is 3-(3-chlolamidopropyl)dimethylammonio-1-propanesulfonate (conveniently known as CHAPS) or 3-(3-chlolamidopropyl)dimethylammonio-2-hydroxyl-1-propanesulfonate (conveniently known as CHAPSO), or mixtures thereof.

In particular, we have found that an especially effective extraction of lipopolysaccharide antigen from Chlamydia species such as *Chlamydia trachomitis, C. psittaci* and *C. twar*, is achieved if the extraction is performed using an aqueous solution of a zwitterionic surface active agent, especially CHAPS and/or CHAPSO.

We have also found that an especially effective extraction of a proteinaceous antigen from *Neisseria gonorrhoeae* is achieved if the extraction is performed using an aqueous solution of a zwitterionic surface active agent, especially CHAPS and/or CHAPSO.

Preferably, the extraction is conducted at elevated temperature, for example in excess of about 50° C., for a period of time sufficient to solubilise the antigenic material. More preferably, the extraction temperature is at least about 60° C. In general, the extraction temperature need not be greater than about 100° C., and is preferably not greater than about 90° C. Ideally, the extraction temperature is about 80° C. The stage of the extraction conducted at such elevated temperature should generally last for at least about 5 minutes.

Preferably, the quantity of surface active agent in the aqueous extraction medium is at least about 0.1% by weight. Preferably the quantity of surface active agent is not greater than about 2%, and more preferably not greater than about 1% by weight.

The pH of the extraction medium should generally be in the range of about 7.5 to about 9.

As stated above, the extraction medium should be substantially free from divalent cations. In particular, zinc and magnesium ions should not be present in any appreciable quantity. This can be achieved by using ion-free water and other components when preparing the extraction medium. Alternatively, or in addition, chelating agents such as EDTA, EGTA or DPTA can be incorporated in the extraction medium to remove, in effect, any divalent cations that may be present. If the performance of the subsequent assay applied to the extracted antigen solution may be adversely influenced by ionic strength, it is preferable that the chelating agent is used in the free acid form, rather than as a water-soluble salt such as its sodium salt; this appears to be an important consideration in the case of extraction from Neisseria. We believe that the effective absence of divalent cations enhances disruption of epithelial cellular material which in turn enhances extraction of any bacteria such as Chlamydia which is an intra-cellular parasite.

In a typical extraction procedure according to the invention, a biological sample obtained from a patient suspected of carrying a Chlamydia infection, for example, is contacted with an extraction medium containing the CHAPS and/or CHAPSO. Appropriate samples can take the form, for example, of genital, rectal or ocular swabs, or centrifugal pellets from liquids such as early morning urine. Extraction, for example at 80° C. for 10 minutes, is followed by a brief period, for example 5 minutes, during which the extraction medium is allowed to cool. Thereafter the extraction medium can be separated from solid matter, for example by removal of the swab and filtration of the solution to provide a sample liquid containing any extracted antigen ready for use in any suitable assay procedure. The subsequent assay can involve any conventional assay technique, such as radioimmunoassay or enzyme-linked immunoassay. The extracted sample is ideal for use in an immunochromatographic assay procedure such as described and claimed in GB 2204398 A, especially using a nitrocellulose solid phase and an antibody reagent labelled with a direct particulate label such as coloured latex particles. The use of the CHAPS and/or CHAPSO enhances the sensitivity of a Chlamydia assay which involves anti-lipopolysaccharide antigen antibodies as specific binding reagents.

EXAMPLE 1

An extraction procedure for *Chlamydia trachomatis* can be performed as follows. This provides an extract suitable for use in an immunoassay.

The extraction procedure utilises:

a) Disposable, flexible plastics "test tubes" each capable of holding a volume (e.g. 5 ml) of liquid and of accommodating the end of a conventional sampling swab.

b) A heating block in which such tubes can be inserted to permit the contents of the tube to be heated to a temperature in the range 50°–100° C. and held at that temperature for at least a number of minutes.

c) Means for filtering the liquid contents of the tube at the end of the extraction procedure. Conveniently this can take the form of a filter plug incorporated in a perforated stopper with which the tube can be closed and through which the liquid contents can be expelled.

d) An extraction buffer having the following formulation:

0.1M TRIS pH 8.5 containing
   0.85% Sodium chloride
   0.25% CHAPSO
   1% Bovine serum albumin
   5 m M EDTA To conduct the extraction, a pre-determined quantity (for example 600 μl) of extraction buffer is placed in a tube. A genital swab from a patient suspected of carrying a Chlamydia infection is placed in the tube, and the tube and contents are then incubated in the heating block at a temperature of approximately. 80° C. for 10 minutes. The tube is removed from the heating block and allowed to cool for 5 minutes. The swab is lifted out of the extraction buffer and, before the swab is removed completely from the tube, the sides of the tube are pressed in gently by hand to squeeze liquid from the swab. The swab can then be removed completely from the tube and discarded. A perforated stopper containing a filter plug is inserted in the top of the tube, and the liquid contents of the tube can be expelled therethrough to provide an essentially clear liquid sample containing any extracted Chlamydia lipopolysaccharide antigen for use in a subsequent assay. If desired, one or more assay reagents, such as labelled antibodies, can be added to the contents of the tube before the filter/stopper is applied to the tube.

EXAMPLE 2

The same extraction procedure as Example 1 is followed. However, the extraction buffer has the formulation:

0.1M TRIS pH 8.5 containing:
1.25% Sodium Chloride
0.25% CHAPSO
1% Bovine Serum Albumin
5 m M EDTA
10 m M L. Ascorbic Acid.

An increased level of sodium chloride helps to prevent non-specific binding, which may occur in the subsequent immunoassay. The presence of ascorbic acid (preferably L form) has been found to increase the storage life of the extraction buffer, where it acts as a stabilizer, when the buffer is subjected to adverse conditions (e.g. increased temperature during distribution, or long-term refrigerated storage).

We claim:

1. A procedure for extracting solubilized lipopolysaccharide antigen from *Chlamydia trachomatis, C. psittaci* or *C. twar* cellular material or proteinaceous antigen from *Neisseria gonorrhoeae* cellular material which comprises treating the cellular material with an aqueous extraction solution with a pH of about 7 to 9 containing at least about 0.1% by weight of CHAPS, CHAPSO or mixtures thereof, together with bovine serum albumin, EDTA, ascorbic acid and sodium chloride, in the absence of divalent cations and at a temperature in excess of about 50° C. for at least about 5 minutes sufficient to solubilize the antigen and recovering the thus solubilized antigen.

2. The process of claim 1 wherein the antigenic material is *Neisseria gonorrhoeae* antigen.

* * * * *